*(12)* United States Patent
Pozzato et al.

*(10)* Patent No.: US 11,975,122 B2
*(45)* Date of Patent: May 7, 2024

(54) PREPARATION METHOD FOR REVITALIZING A BIOCOMPATIBLE TISSUE

(71) Applicant: Telea Biotech S.R.L., Sandrigo (IT)

(72) Inventors: Gianantonio Pozzato, Vicenza (IT); Maurizio Marzaro, Treviso (IT)

(73) Assignee: Telea Biotech S.R.L., Sandrigo (IT)

( * ) Notice: Subject to any disclaimer, the term of this patent is extended or adjusted under 35 U.S.C. 154(b) by 531 days.

(21) Appl. No.: 17/284,579

(22) PCT Filed: Mar. 6, 2020

(86) PCT No.: PCT/IB2020/051947
§ 371 (c)(1),
(2) Date: Apr. 12, 2021

(87) PCT Pub. No.: WO2020/178792
PCT Pub. Date: Sep. 10, 2020

(65) Prior Publication Data
US 2021/0386913 A1    Dec. 16, 2021

(30) Foreign Application Priority Data
Mar. 7, 2019   (IT) ......................... 102019000003299

(51) Int. Cl.
*A61L 27/36*   (2006.01)
*A61L 27/38*   (2006.01)

(52) U.S. Cl.
CPC ....... *A61L 27/3691* (2013.01); *A61L 27/3679* (2013.01); *A61L 27/38* (2013.01); *A61L 2430/22* (2013.01); *A61L 2430/40* (2013.01)

(58) Field of Classification Search
None
See application file for complete search history.

(56) References Cited

U.S. PATENT DOCUMENTS 5,112,354 A    5/1992    Sires

FOREIGN PATENT DOCUMENTS

WO    2008/146106 A2    12/2008
WO    2011/051793 A1    5/2011

OTHER PUBLICATIONS

International Search Report and Written Opinion dated May 28, 2020, issued in PCT Application No. PCT/IB2020/051947, filed Mar. 6, 2020.
Maurizio Marzaro et al., *Autologous Satellite Cell Seeding Improves in Vivo Biocompatibility of Homologous Muscle Acellular Matrix Implants*, International Journal of Molecular Medicine, Jan. 1, 2002, pp. 177-182, XO055648314.
Silvia Baiguera et al., *Tissue Engineered Human Tracheas for in Vivo Implantation*, Biomaterials, Elsevier Science Publishers, vol. 31, No. 34, Dec. 1, 2010, pp. 8931-8938, XP027381055.
Maurizio Marzaro et al., *In Vitro and In vivo Proposal of an Artificial Esophagus*, Journal of Biomedical Materials Research, part A, vol. 77, No. 4, Jun. 1, 2006, pp. 795-801, XP002694600.
Thorsten Walles et al., *Experimental Generation of a Tissue-Engineered Functional and Vascularized Trachea*, Journal of Thoracic and Cardiovascular Surgery, vol. 128, No. 6, Dec. 1, 2004, pp. 900-906, XP00466134.

*Primary Examiner* — Michael V Meller
(74) *Attorney, Agent, or Firm* — Workman Nydegger

(57) ABSTRACT

A method for preparing a biocompatible tissue for revitalization thereof, wherein such tissue has an essentially tubular shape. The method provides inserting a support that mainly extends along a longitudinal extension axis inside the cavity defined by the tissue and performing on the outer and/or inner surface of the tissue a plurality of holes spread out on at least one of the generatrixes of the tissue. Holes are made with a depth which occupies at least a part of the thickness of the tissue.

8 Claims, 6 Drawing Sheets

PREPARATION METHOD FOR REVITALIZING A BIOCOMPATIBLE TISSUE

BACKGROUND OF THE INVENTION

1. The Field of the Invention

The invention relates to a preparation method for revitalizing a biocompatible tissue and a device configured for realizing the aforesaid method.

2. The Relevant Technology

There exist several clinical situations which require replacing a tubular-shaped organ, such as for example trachea, intestine or oesophagus, whose functionality is impaired for several reasons.

In order to make such replacements, the most up-to-date surgery approaches provide to use biocompatible tissues, generically called "scaffolds", consisting in an extracellular matrix obtained from the decellularization of a matrix of allogenic, xenogenic or even synthetic origin. These scaffolds, following an accurate re-cellularization with stem cells or autologous differentiated cells, are grafted in human beings serving as inductive patterns for reconstructing the tissue or the impaired organ.

The tissue technology using allogenic or xenogenic matrices usually consists in removing cells from biological tissues by means of physical, enzymatic or chemical processes, without causing biological, mechanical or composition alterations of the extracellular matrix, so as to obtain original tissue specific-protein scaffolds provided with an intact base structure but which, however, are not immunogenic.

Subsequently, cells belonging to the subject receiving the graft are introduced in such scaffolds to make them reproduce and regenerate the tissue which will be then grafted in the human being or other biological substances adapted to promote a rapid tissue regeneration, such as for example platelet lysates, hyaluronic acid, Platelet-Rich Plasma, growth factors, cytokines and amniotic membrane.

There exist several known techniques to realize a scaffold from donor-collected tissues.

In particular, in the European Patent EP 2164536 to the Applicant, a particularly effective method for preparing re-cellularization of an organic tissue is disclosed.

Such method consists in arranging an acellular tissue on a plane and making a plurality of holes on the tissue surface adapted to receive the live cells to be re-grafted.

In particular, when the organic tissue to be treated has a tubular shape, the latter is cut along the main extension direction so that it can be opened and outstretched on the plane working surface such as the bottom of a Petri dish or similar.

On the outstretched cut tissue the aforesaid holes are then made by means of one or more metal needles that are connected to a power supply source whose function is to generate on the tip of each needle the passage of a current with such an intensity and waveshape as to provide enough energy for breaking bonds joining the molecules of the organic tissue, thus obtaining the aforesaid holes.

The energy used has such an intensity as to limitedly allow to break the bonds between molecules concerned by the passage of current, while in the surrounding area no effect, such as break, tear, necrosis, reduction or increase of thickness, alteration of the liquid content, coagulation nor other degenerative effect takes place.

Subsequently, host cells are seeded on the tissue where, due to such holes, they will go in depth and take root on the walls of holes thereof for later multiplying and extremely rapidly revitalizing all the organic tissue.

Once revitalized, the organic tissue is closed by means of suturing by a specialized surgeon to reform the organ functional tubular shape and enable engraftment thereof in the human being.

However, such method has some drawbacks.

In particular, when the acellular tissue has no planar shape it must necessarily be cut and opened to be pierced throughout its own surface, ensuring a subsequent uniform cell seeding and regrowth.

Such operations must necessarily be carried out in a sterile environment and with sterile equipment to avoid any type of contamination.

Further, after seeding, being suturing of the cut-tissue edges necessary, it will be required to provide a minimum loose tissue at the cut edges where such stitches will be placed, thus limiting the actual surface of tissue where it will be possible to make holes and hence seed cells.

In addition, proper attention, care and specific manual skill are required for manipulating and treating a sutured tissue in order to prevent its degeneration.

Still inconveniently, the part of tissue submitted to suturing will differ from the surrounding tissue in that, as it is a scar tissue, it contains less elastic fibres, thus determining its prejudicial hardening.

SUMMARY OF THE INVENTION

The object of the present invention is therefore to realise a preparation method for revitalizing a biocompatible tissue which overcomes the mentioned drawbacks.

More specifically, it is the object of the present invention to realise a method for preparing the tissue that is capable of revitalizing it with no need to cut and suture it as it happens in the prior art.

Furthermore, it is an object of the invention to realise a preparation method for revitalizing a tissue that does not lead to growth of scar tissue in the tissue to be grafted into the human being.

Still, it is the object of the invention to realise a method for preparing the tissue such that, in case the latter is revitalized by introducing cells, these latter are eased in entering and colonizing the tissue.

Furthermore, it is an object of the invention that the aforesaid method enables to prepare a tissue where biological substances with a regenerating function can easily be absorbed by the tissue itself.

Further, it is the object of the present invention to realise a device that enables to perform the aforesaid method in a reproducible manner, such to ensure high repeatability.

Not least, it is the object of the invention to realise a device which enables to rapidly perform such preparation method.

The aforesaid objects are reached by a method for preparing a biocompatible tissue for revitalization which provides to use an essentially tubular-shaped biocompatible tissue.

In particular, the method of the invention provides inserting a support extending mainly longitudinally inside the cavity defined by the aforesaid tubular-shaped biocompatible tissue and making on the outer and/or inner surface of such tissue one or more holes, spread out on at least one of the generatrixes of such tissue, with such a depth as to occupy at least a part of the thickness of the tissue, as indicated in the main claim.

The objects of the present invention are further reached by a device comprising one or more conductive needles arranged on a mechanical standing and a longitudinal extension support adapted to be inserted in the cavity defined by a biocompatible tissue with essentially tubular shape, configured to realise the method of the invention, as indicated in the claims.

Further characteristics of the method and device are described in the dependent claims.

BRIEF DESCRIPTION OF THE DRAWINGS

The aforementioned objects, together with the advantages which will be mentioned below, will be better highlighted during the description of some preferred embodiments of the invention which are given, by way of non-limiting example, with reference to the appended drawings, where.

DETAILED DESCRIPTION OF THE PREFERRED EMBODIMENTS

According to one first embodiment of the invention, the method provides to prepare a tissue 6 made of biocompatible material of an essentially tubular shape for revitalization.

It is specified that the term "biocompatible" means the capacity of a material to be in contact with a living system without causing adverse effects, as reported in "Terminology for biorelated polymers and applications (IUPAC Recommendations 2012)", Pure Appl. Chem., Vol. 84, No. 2, pp. 377-410, 2012.

Preferably, such biocompatible tissue 6 is an organic tissue, more preferably an organic tissue of animal origin so that it can be advantageously used for research in the regenerative surgical field of animal tissues, intended for human graft.

Still preferably, such animal tissue is a tissue of porcine origin due to the known tissue and genetic similarity between the human being and such animal.

However, it is not excluded that, according to alternative embodiments of the invention such organic tissue is of human origin.

Still, it is not excluded that the biocompatible tissue 6 is of synthetic origin, such as—as a non-limiting example—a tissue made of poly(lactic-co-glycolic)acid.

According to the first embodiment of the invention, the biocompatible tissue 6 is furthermore an acellular tissue.

The term "acellular" means a tissue, generally of organic type, called scaffold, which has been previously treated by means of physical, enzymatic or chemical processes already known to obtain an organic tissue without cells and without causing biological, mechanical or composition alterations of the extracellular matrix.

It is not excluded that, according to variant embodiments of the invention, the biocompatible tissue 6 is a cellularized tissue, i.e., a tissue containing a set of structurally similar cells.

Figure 2:
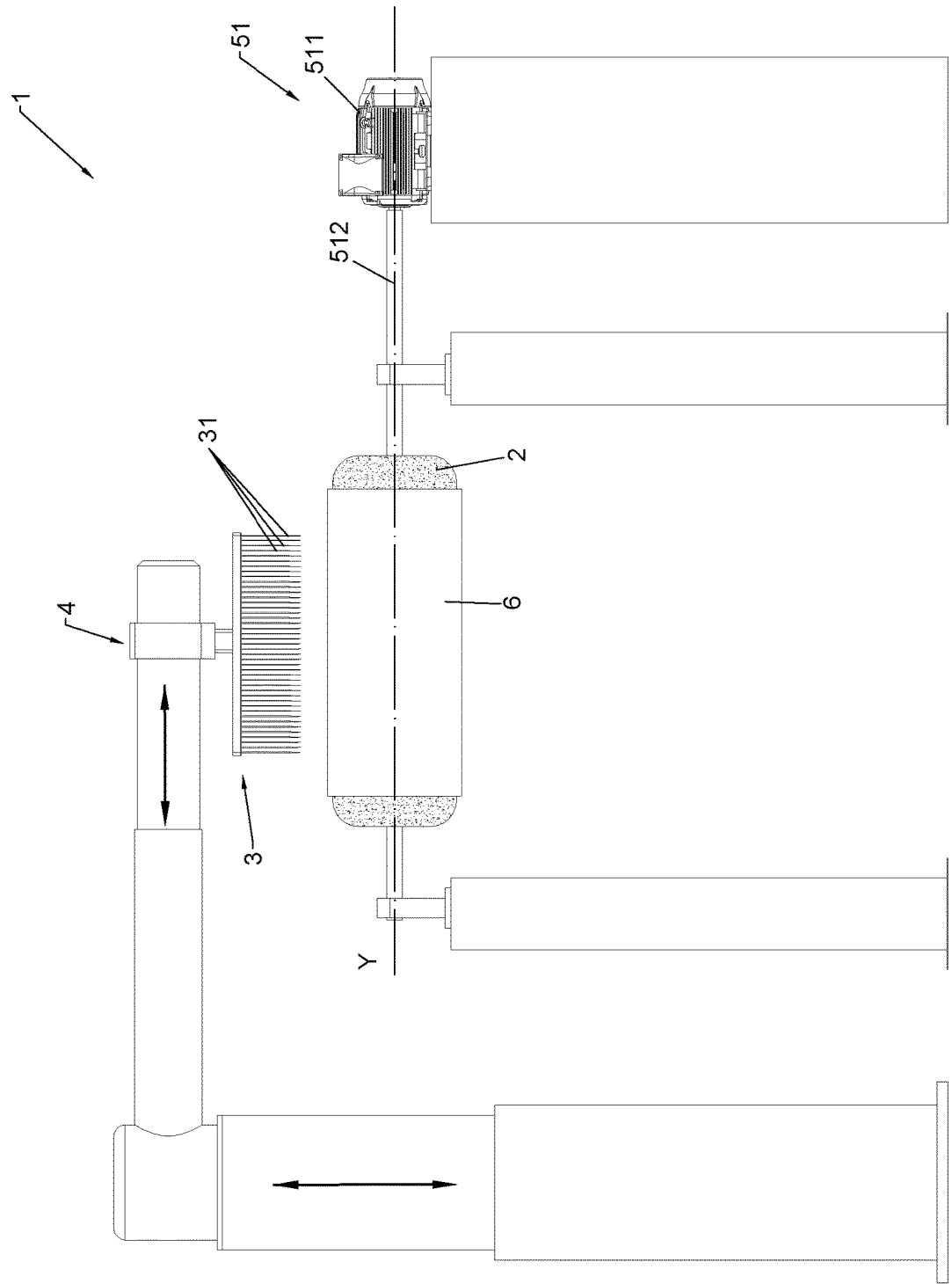
in FIGS. 2 to 6 they are shown in sequence and schematically operations of the preparation method for revitalization according to one first embodiment of the present invention.

According to the first embodiment of the method of the invention, schematically shown in FIGS. 2 to 6, a support 2 that mainly extends along a longitudinal extension axis Y is inserted inside the cavity defined by the essentially tubular-shaped tissue 6, as shown in FIG. 2.

It is specified that the support 2 is configured to support the tissue 6 such that the latter advantageously maintains its tubular shape during the following operations of the method according to the invention.

Preferably, such support 2 is an essentially cylinder-shaped support with a substantially circular section.

Furthermore, it is specified that such tubular support 2 can be hollow or full.

It is not excluded that, according to alternative embodiments of the invention, such support extends along a longitudinal extension axis and has a section that is octagonal, hexagonal, etcetera or has an ellipsoid shape, as long as the aforesaid support has a shape that is suitable to be inserted inside the cavity of the tubular tissue 6.

Figure 3:
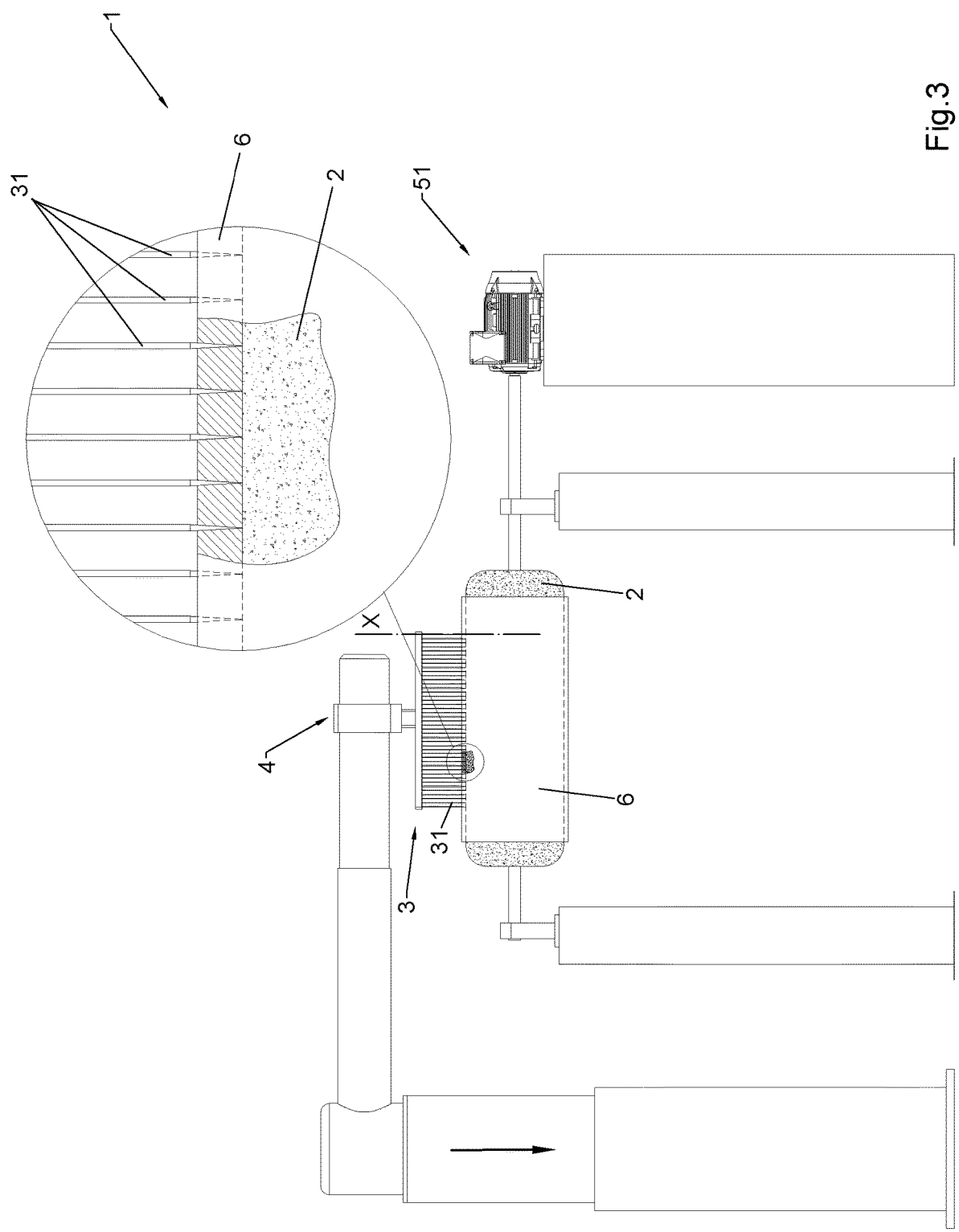

Once the tissue 6 is arranged on the aforesaid support 2, the method provides to realise on the outer and/or inner surface of the tissue 6 one or more holes 61 with such a depth as to occupy at least part of the thickness of the tissue 6, preferably throughout the thickness of the tissue 6, as schematically shown in FIG. 3.

Such holes 61 are spread out on at least one of the generatrixes of the tissue 6.

It is specified that such holes 61 can be spread out on a single or on a plurality of generatrixes of the aforesaid tissue 6.

Such holes 61 can further be spread out on each of such generatrixes in a similar or different number, and further according to an ordered or random trend.

Advantageously, the method of the invention allows to prepare a tissue to be revitalized with no need to cut the aforesaid tissue 6, as required by the known methods.

Thereby the need to suture the tissue for forming a tissue tubular three-dimensional structure before grafting is advantageously avoided.

Further, advantageously, making a plurality of holes enables the tissue to become particularly receptive to cells which can be seeded on the aforesaid tissue 6 and enter easily into the latter, encouraging colonization of the matrix of fibres of the connective tissue and thus speeding the re-colonization process.

Further, the presence of such a plurality of holes enables the tissue to easily absorb therein substances with a regenerating function.

According to the first embodiment of the method of the invention, such holes 61 are made by means of one or more conductive needles 31, particularly needles made of conductive material, preferably of metal material.

In particular, such holes 61 are made by means of a device 1, which will be later described in detail, wherein the aforesaid needles 31 are connected to a power supply source 4 which causes the passage of a current on the tip of each needle 31.

The intensity and the waveshape of the passage of current are such to provide enough energy to break the bonds that join the tissue molecules at the tip of the needle so that such passage of current makes each hole of such dimensions as to let the tip of the needle enter in the space created by the opening of molecular bonds.

Thereby, advantageously, making holes on the tissue does not cause any alteration of tissue, in particular of the connective tissue surrounding the hole, such as for example necrosis, coagulation, tears, and so on.

Still advantageously, making holes according to the invention does not cause fusion, necrosis or coagulation not even of the protein material forming the tissue. On the edges of the aforesaid holes several cavities, fissures, leakages or natural communications between the lumen of the hole and the surrounding matrix are thus formed. These cavities enable to make a plurality of communications between the holes and the surrounding connective tissue through which cells can spread out inside the connective tissue, resulting in three-dimensional cell cultures inside the latter.

Qualitatively, the best results are obtained when conductive needles 31 are supplied with an alternating power voltage with a frequency equal to or greater than about 4 MHz.

Such frequency produces a passage of current that is high enough to break the bonds between the tissue molecules without deteriorating the surrounding tissue.

The frequency of about 4 MHz is preferred.

It is not excluded that, according to alternative embodiments of the invention, the aforesaid holes 61 in the tubular tissue 6 can be made by means of needles supplied with a power voltage with a frequency lower than 4 MHz.

Still, it is not excluded that according to variant embodiments of the invention holes 61 can be made by means of methods that differ from what indicated, as long as making holes 61 does not result in the degradation of the tissues surrounding the hole and in any case of the biocompatible tissue in general.

Figure 4:
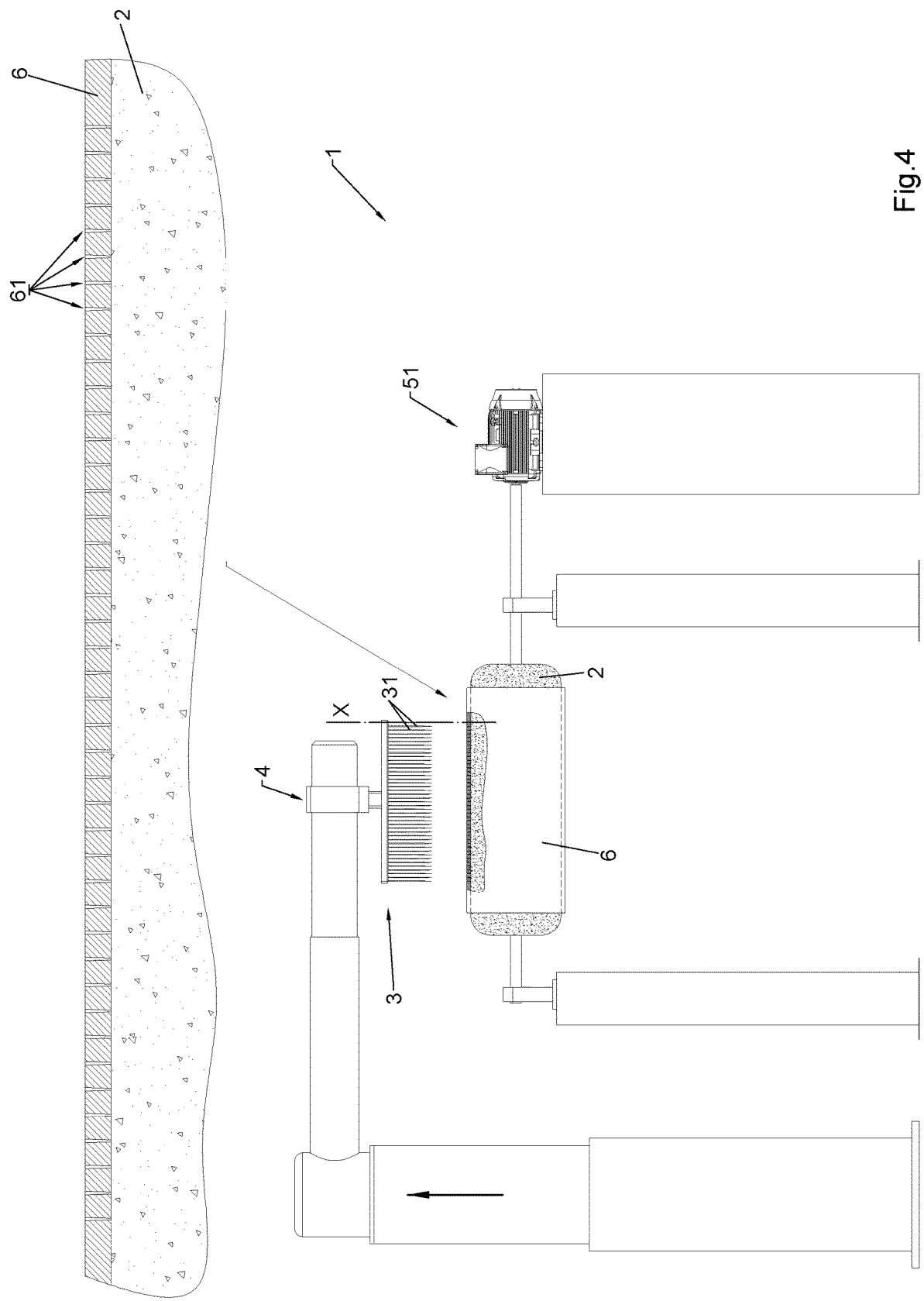

According to the first embodiment of the method of the invention, during the piercing operation, the support 2 with the tissue 6 is rotated according to its own longitudinal extension axis Y, as shown in FIG. 4.

Preferably, the support 2 with the tissue 6 is rotated according to a discrete-type sequence of movements according to axis Y.

Each of such rotation movements has a predefined angular width, preferably of fraction of degree, so as to suitably regulate and control the piercing operation and therefore the spreading out of holes 61 on the tissue 6.

The term "predefined" means that the angular width of each rotation movement is selected by the person performing the method according to the characteristics of the tissue being treated and by the intended distribution of the holes.

Further, it is specified that the rotation movements can have an angular width with a value that is equal or different between them.

Figure 5:
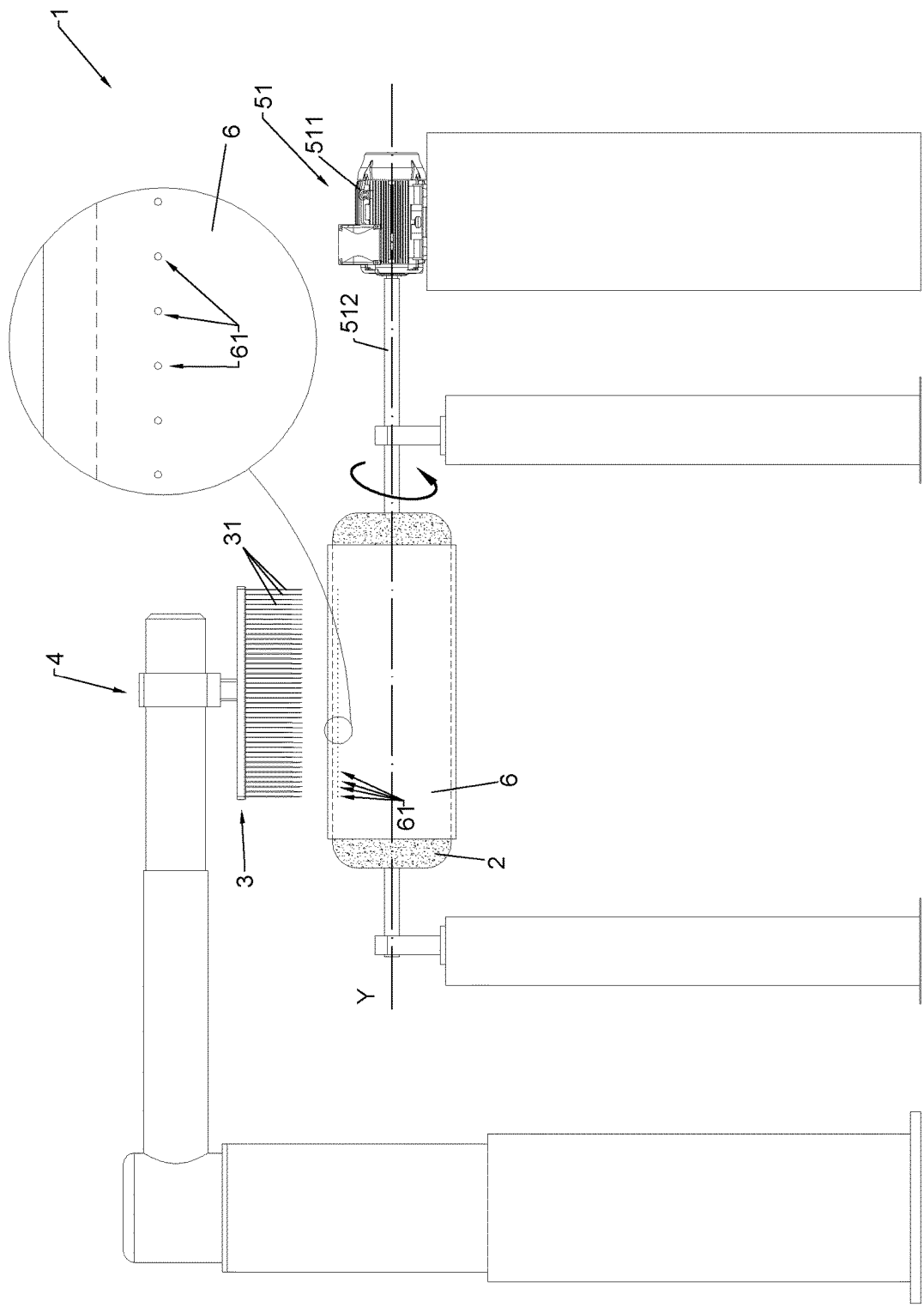

Hence, operatively, once a first plurality of holes 61 are made along a generatrix of tissue 6 supported by support 2, needles 31 are taken away from the tissue 6 and the support 2 is rotated along its own axis Y, as shown in FIGS. 4 and 5.

Figure 6:
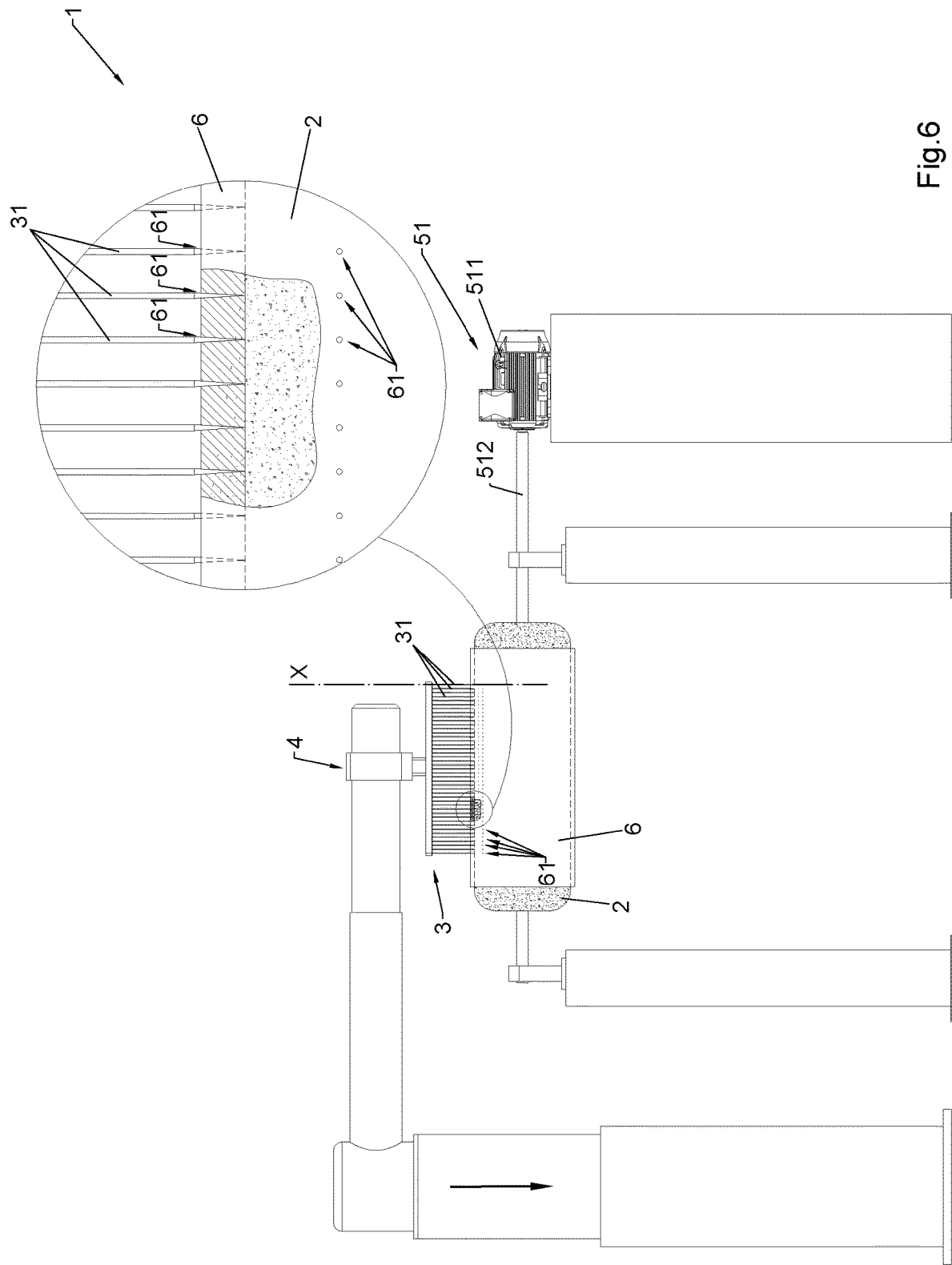

After rotating the support 2, needles 31 are again moved towards the tissue 6 to make a new plurality of holes 61 at a new generatrix of tissue 6, that is different from the previous one, as illustrated in FIG. 6.

Such operations of rotating the support and piercing the tissue are repeated until a plurality of holes is made along each of the tissue generatrixes.

Advantageously, the rotation of support 2 and consequently of the tubular tissue 6 arranged thereon allows to ease and speed up making holes 61 along all the generatrixes of the tissue according to its natural three-dimensional shape, ensuring a uniform spreading out of holes throughout the tissue surface.

In particular, experiments carried out by the Applicants have shown that combining the use of needles 31 with a very low diameter and the rotation of the support during the piercing operation allows to make up to 1000-1600 holes per $cm^2$ of tissue.

According to the first embodiment of the method of the invention, once the piercing operations on one or more of the generatrixes of tissue 6 are finalized, as indicated above, the tissue 6 can be extracted from the support 2 by means of suitable surgery grippers and arranged entirely on a Petri dish, or similar container, into which cells, preferably live cells, which will revitalize the tissue itself are introduced and/or other biological substances with regenerating function are introduced.

Cells that are introduced by means of holes 61 present in the tissue and spread out evenly on the surface of the latter, will easily be able to colonize the tissue matrix and guarantee a complete and even revitalization of the tissue itself.

It is not excluded that, according to alternative embodiments of the method of the invention, following the piercing operation, the pierced tubular tissue 6 is not extracted from the support 2 but is in contrast treated with cells and/or the aforesaid substances directly on the support 2, for instance soaking the tissue 6 with the support 2 still inserted therein into a culture medium that is suitable to allow the cell growth, thus maintaining the natural three-dimensional shape of the tubular tissue 6 even during the seeding and revitalization operation.

Still, it is not excluded that according to variant embodiments of the method of the invention the pierced tubular tissue 6 can be used as it is to be grafted on the animal or patient, namely, it is not excluded that the pierced tubular tissue 6 is not treated with cells and/or biological substances by the operator before being grafted in the host body, and hence cells of the animal or patient that are already in situ will be those to colonize and revitalize the grafted tubular tissue 6.

Part of the invention is also a second embodiment of the invention, not shown in the figures, which comprises all the characteristics indicated for the first embodiment of the invention, including the variants, except that during the piercing operation the support 2 of the tissue 6 is not rotated as indicated above, but it is fixed.

According to such second embodiment, the method provides that during the piercing operation conductive needles 31 are moved according to a revolution axis substantially corresponding to the longitudinal extension axis Y of the support 2.

Such movement of the needles 31 is advantageously made according to a discrete-type sequence of movements that enable needles 31 to be moved along the outer and/or inner surface of the tissue 6 supported by support 2 to make the aforesaid plurality of holes 61 along one or more generatrixes of the tissue thereof.

Such movement of needles 31 combined with the piercing operation by conductive needles thereof allows to make holes 61 along each generatrix of the tissue 6 with no need to modify its natural three-dimensional tubular shape, ensuring an even spreading out of the holes throughout the tissue surface.

Part of the invention is a third embodiment of the method of the invention that comprises all the characteristics indicated for the first embodiment of the invention, including the variants, and that also provides that conductive needles 31 are moved according to a revolution axis substantially corresponding to the longitudinal extension axis Y of the support 2 during the piercing operation.

More specifically, according to such third embodiment of the invention, during the piercing operation, the support 2 is rotated preferably according to a discrete-type sequence of movements and predefined angular width according to its own longitudinal extension axis Y and, furthermore, conductive needles 31 are moved about the support 2 according to a revolution axis substantially corresponding to axis Y and preferably according to a discrete-type sequence of movements.

In particular, the rotation movement of the support 2 and the revolution movement of the conductive needles 31 will be synchronized between them so that piercing the tissue 6 is evenly made on each generatrix of the tissue 6, without modifying its three-dimensional structure.

Further characteristics of the invention will be better highlighted in the description of a device configured to implement the method of the invention.

Figure 1:
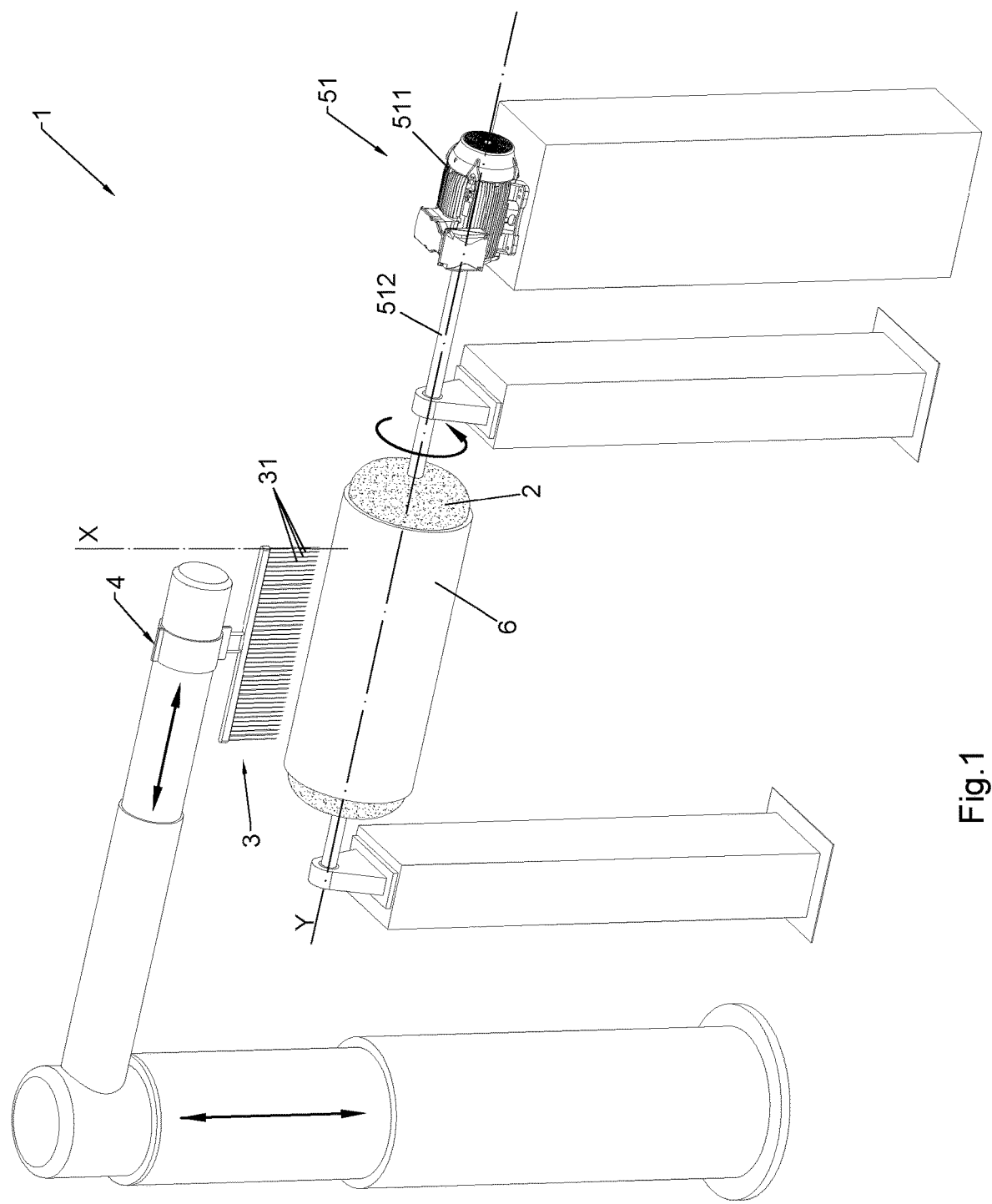
in FIG. 1 it is schematically represented an axonometric projection of a device according to a first embodiment of the invention.

In particular, in FIG. 1 a non-limiting example of a device according to a first embodiment of the invention is shown that allows to perform the method according to the previously-described first embodiment of the invention.

The device according to the first embodiment, referred to as number 1, is configured to make one or more holes 61 on the surface of a biocompatible tissue 6 for revitalization thereof.

The device 1 comprises a support 2 that mainly extends along a longitudinal extension axis Y which is configured to be inserted inside the cavity defined by an essentially tubular-shaped biocompatible tissue 6.

Such support 2 is adapted to support the tissue 6 such that the latter maintains its natural three-dimensional tubular shape.

As indicated for the method of the invention, the tubular biocompatible tissue 6 can be of organic or synthetic origin.

Such tissue 6 is preferably an organic tissue, more preferably an acellular organic tissue.

Returning to the device according to the first embodiment of the invention, the support 2 is an essentially cylinder-shaped support with a substantially circular section It is not excluded that, according to alternative embodiments of the invention, such support has a longitudinal extension with a section that is octagonal, hexagonal, etcetera or has an ellipsoid shape, as long as such shape is suitable to allow inserting the support inside the cavity defined by the tubular tissue 6.

The device 1 further comprises a plurality of conductive needles 31 arranged on a mechanical standing 3.

Such conductive needles 31 are preferably made of metal material.

Preferably, such conductive needles 31 have a diameter that is slightly higher than or equal to the diameter of cells that could be re-grafted in the tissue.

As shown in FIG. 1, such conductive needles 31 are preferably orderly arranged on the mechanical standing 3 to preferably create at least an ordered row, parallel to the longitudinal extension axis Y of the support 2.

Preferably though not necessarily, needles 31 are arranged equally spaced apart between them to form the aforesaid row.

However, it is not excluded that, according to alternative embodiments of the invention, such plurality of needles 31 is not arranged in an ordered row parallel to the longitudinal extension axis Y but rather according to any geometrical shape, for example, circular, elliptical or according to a matrix, or that such device 1 comprises a single needle 31.

Further, the aforesaid needles 31 are directed towards the outer surface of the support 2 so as to make a plurality of holes 61 spread out on at least one of the generatrixes of the aforesaid tissue 6.

In order to make such plurality of holes 61, the mechanical standing 3 can be moved according to the extension direction X of the needles 31 approaching to or moving away from the tissue.

In particular, the mechanical standing 3 moves according to the direction X approaching the tissue 6 during the piercing operation of the method of the invention and, when the tip of the needle contacts the surface of the tissue, it moves with such a speed at to pierce the tissue 6 for making a hole 61 without degrading the tissues surrounding the hole itself or in any case the tissue in general.

Advantageously, the movement of the mechanical standing 3 can be adjusted such that the hole 61 is made with a depth which occupies at least a part of the thickness of the tissue 6, preferably throughout the thickness of the tissue, so as to obtain the above-mentioned advantages.

Preferably, the mechanical standing 3 can be moved also according to the direction defined by the longitudinal extension axis Y of the support 2, so that it can advantageously be positioned at each point belonging to one of the generatrixes of the tissue 6 and enable making holes 61 throughout the length of the tissue.

It is not excluded that, according to an alternative embodiment of the device of the invention, needles 31 are arranged inside the cavity defined by the tissue 6 and are directed towards the inner surface of the support 2 so as to make the plurality of holes 61 along the inner surface of the tissue 6. In such alternative embodiment of the device, the support 2 is hollow inside so as to house the mechanical standing 3. Further, according to such alternative embodiment, the support 2 has on its own surface one or more pass-through openings that are configured to let needles 31 reach the inner surface of the tissue 6 supported by the support 2 and to make holes 61.

Returning to the first embodiment of the device of the invention, it further comprises a power supply source 4 connected to needles 31 and adapted to provide the tip of each needle 31 with a power current whose intensity and waveshape are such to provide enough energy to cause opening of bonds of the molecules of the tissue 6 that contact the tip of the needle 31.

The power energy provided by the power supply source 4 is preferably non-modulated; however, it is not excluded that according to variant embodiments of the invention such power energy is modulated.

Such power supply source 4 preferably consists in a voltage generator, preferably until a 1500 Volt peak, more preferably a 30-500 Volt peak-peak, still more preferably a 200-230 Volt peak-peak, with a wave frequency higher than or equal to 4 MHz, preferably of about 4 MHz.

It is not excluded that, according to variant embodiments of the device of the invention, the wave frequency is lower than 4 MHz.

Preferably but not necessarily, such wave is a type of distorted sinusoidal wave and thus with harmonics.

Such harmonics are preferably at least of the first, second and third order.

The power of the voltage generator is adjusted such that the current available on the tip of each needle 31 is suitable to make such holes.

According to the first embodiment of the device of the invention, the support 2 is made of conductive material, so that it advantageously allows the passage of the current to make the plurality of holes 61 on the tissue 6 according to what previously indicated and reaching the advantages set forth above.

The preferred conductive material is agar gel since such material is advantageously a conductor and can further be shaped based on size and shape of the cavity of the tubular tissue 6 to be prepared for revitalization, within which it is inserted.

Furthermore, agar gel is an easily commercially available material.

It is not excluded that, according to alternative embodiments of the invention, such conductive material is a material other than agar gel, or, still, it is not excluded that the material of the support 2 is not a conductive material.

Preferably, the support 2 further comprises a conductive element made of metal material therein, preferably a metal bar, which further promotes the passage of power current from the tip of the needle 61 to the molecules of the tissue 6 while piercing the latter.

According to the first embodiment of the device 1, the support 2 is connected to rotation means 51 configured to allow the support 2 to rotate according to the longitudinal extension axis Y of the support 2.

Preferably, such rotation means 51 are configured to rotate the support 2 according to a discrete-type sequence of movements according to the axis Y.

As shown in FIG. 1, such rotation means 51 comprise an electric motor 511 preferably of the stepper type, connected to the support 2 by means, for example, of a rotation shaft 512.

The rotation of the support 2, and hence of the tissue 6 arranged thereon, combined with the movement of the mechanical standing 3 and of the needles 31 according to direction X allows to obtain an even spreading of holes 61 throughout the thickness and throughout the surface of the tissue 6 to be revitalized.

It is not excluded that, according to different embodiments of the invention, such rotation means 51 and/or such mechanical standing 3 are connected to an electronic control unit which allows to rotate the support 2 and/or move the mechanical standing 3 in sequence according to direction X, in addition to maximum precision.

Part of the invention is also a second embodiment of the device of the invention, not shown in the figures, that is configured to implement the method of the invention according to the second embodiment of the method of the invention, which comprises all the characteristics indicated for the first embodiment of the device, including the variants, except that it does not comprise rotation means 51. Further, in the second embodiment of the device the mechanical standing 3 is configured to be moved according to a revolution axis substantially corresponding to the longitudinal extension axis Y of the support 2.

In particular, according to such second embodiment of the device, the mechanical standing 3 is provided with movement means configured to move such mechanical standing 3 about the support 2 according to a revolution axis substantially corresponding to axis Y, and furthermore to move the standing 3 according to the extension direction X of the needles 31 and, preferably, also according to the direction defined by axis Y of the support 2. Movement of the standing 3 and of needles 31 about the support 2 and hence about the tissue 6 is thereby allowed, according to a discrete-type sequence of movements, enabling needles to be moved throughout the surface of the tissue 6 to make, along one or more generatrixes of the latter, the aforesaid plurality of holes 61.

Part of the invention is also a third embodiment of the device of the invention, not shown in the figures, that is configured to implement the method of the invention according to the third embodiment of the method of the invention, which comprises all the characteristics indicated for the first embodiment of the device, including the variants, and, further, where the mechanical standing 3 is configured to be moved according to a revolution axis substantially corresponding to the longitudinal extension axis Y of the support 2.

In particular, according to such third embodiment of the device, the mechanical standing 3 is provided with movement means configured to move such mechanical standing 3 about the support 2 according to a revolution axis substantially corresponding to axis Y, and furthermore to move the standing 3 according to the extension direction X of the needles 31 and, preferably, also according to the direction defined by axis Y of the support 2. Thereby movement of the standing 3 and of needles 31 about the support 2 and hence the tissue 6 is allowed, according to a discrete-type sequence of movements.

Advantageously, according to such third embodiment of the device of the invention, the support 2 is rotated by means of rotation means 51 according to its own longitudinal extension axis Y as previously indicated and, further, movement means move the mechanical standing 3 according to the aforesaid revolution axis corresponding to the longitudinal extension axis Y of the support, during the piercing operation of the method according to the third embodiment of the method of the invention.

Therefore, based on the above, the present invention has reached all of the predetermined objects.

In particular, thanks to the use of a tubular-shaped biocompatible tissue, the object of implementing a preparation method for revitalizing a tissue with no need to cut it and thus to suture it prior to grafting is reached.

Further, the preparation method for revitalizing a tissue of the invention does not result in growth of scar tissue in the tissue to be grafted.

Still, the preparation method of the tissue of the invention allows to realise a tissue scaffold in which cells and/or biological substances with regenerating function can easily enter and colonize the tissue.

Furthermore, the device of the invention enables to perform the aforesaid method in a replicable way, ensuring a high repeatability and rapidity in realising such method.

The invention claimed is:

1. A method for preparing a biocompatible acellular tissue for revitalization thereof, said acellular tissue having a tubular shape, said method comprising the following steps:
   a. inserting a support that mainly extends along a longitudinal extension axis inside a cavity defined by said acellular tissue; and
   b. forming on an outer and/or inner surface of said acellular tissue one or more holes spread out on at least one generatrixes of said acellular issue, said one or more holes being made with a depth which occupies at least a part of a thickness of said acellular tissue and being made by one or more conductive needles, and wherein the support is rotated about said longitudinal extension axis during said step b.

2. The method according to claim 1, wherein said acellular tissue is an organic acellular tissue.

3. The method according to claim 1, wherein said support is rotated according to a discrete-type sequence of movements according to said longitudinal extension axis during said forming step, each of said rotation movements having a predefined angular width.

4. The method according to claim 1, wherein said one or more conductive needles are configured to be moved according to a revolution axis substantially corresponding to said longitudinal extension axis of said support during said forming step.

5. The method according to claim 1, wherein said one or more conductive needles are connected to a power supply source, said one or more holes being made by causing a passage of a current on a tip of each needle whose intensity and waveshape are such to provide enough energy for breaking bonds that join molecules of said acellular tissue near the tip of said one or more conductive needles, each of said one or more holes being caused by said passage of current and having such dimensions as to allow the tip of said one or more conductive needles to enter into a space created by opening said molecular bonds.

6. The method according to claim 1, wherein said one or more conductive needles are supplied with an alternating power voltage with a frequency greater than or equal to 4 MHz.

7. The method according to claim 1, wherein said acellular tissue is a tissue of synthetic origin.

8. The method according to claim 1, wherein revitalization of said acellular tissue is made by reintroducing cells and/or biological substances with a regenerating function into said acellular tissue; said one or more holes receiving said cells and/or biological substances when they are reintroduced.

* * * * *